United States Patent
Frid

(10) Patent No.: US 10,842,606 B2
(45) Date of Patent: Nov. 24, 2020

(54) BIFURCATED 3D FILTER ASSEMBLY FOR PREVENTION OF STROKE

(71) Applicant: FRID MIND TECHNOLOGIES, Isnes (BE)

(72) Inventor: Noureddine Frid, Isnes (BE)

(73) Assignee: FRID MIND TECHNOLOGIES, Isnes (BE)

( * ) Notice: Subject to any disclaimer, the term of this patent is extended or adjusted under 35 U.S.C. 154(b) by 235 days.

(21) Appl. No.: 15/754,063

(22) PCT Filed: Sep. 9, 2016

(86) PCT No.: PCT/EP2016/071311
§ 371 (c)(1),
(2) Date: Feb. 21, 2018

(87) PCT Pub. No.: WO2017/042335
PCT Pub. Date: Mar. 16, 2017

(65) Prior Publication Data
US 2018/0228590 A1    Aug. 16, 2018

(30) Foreign Application Priority Data

Sep. 9, 2015 (EP) .................................... 15020154
Sep. 15, 2015 (EP) .................................... 15020162
Jan. 11, 2016 (EP) .................................... 16150763

(51) Int. Cl.
*A61F 2/01* (2006.01)
*A61L 27/04* (2006.01)
(Continued)

(52) U.S. Cl.
CPC ............. *A61F 2/01* (2013.01); *A61L 27/045* (2013.01); *A61L 27/047* (2013.01); *A61L 27/06* (2013.01);
(Continued)

(58) Field of Classification Search
CPC ...... A61F 2/01; A61F 2/06; A61F 2/07; A61F 2/852; A61F 2/86; A61F 2/88;
(Continued)

(56) References Cited

U.S. PATENT DOCUMENTS 6,673,089 B1   1/2004   Yassour et al.
6,740,112 B2   5/2004   Yodfat et al.
(Continued)

FOREIGN PATENT DOCUMENTS

EP   1248372 A2   10/2002
EP   2987463 A1   2/2016
(Continued)

OTHER PUBLICATIONS

Charalambous et al., "Reduction of cerebral embolization in carotid angioplasty: an in-vitro experiment comparing 2 cerebral protection devices", J. Endovasc. Ther., Apr. 2009, vol. 16, issue 2, pp. 161-167, Copyright The International Society of Endovascular Specialists (2009); www.jevt.org.
(Continued)

*Primary Examiner* — Darwin P Erezo
*Assistant Examiner* — Christian D Knauss
(74) *Attorney, Agent, or Firm* — Blue Filament Law PLLC

(57) ABSTRACT

An implantable permanent filter assembly (1) for deployment in a bifurcated vessel includes a main vessel and at least two branches. This assembly includes a filtering sleeve (2) formed of an expendable braided framework (20) able to expand from a radially compressed state in a delivery configuration to a radially expanded state. The filtering sleeve extends along an axis and defines a cylindrical lumen devoid of impermeable layer, having a distal end configured to extend toward the branches of the bifurcated vessel and a proximal end configured to extend toward away from the (Continued)

(INV)

branches of the bifurcated vessel. The braided framework has a plurality of mesh layers (22,23,24) of wires (25) made of biocompatible material, forming a lattice with a plurality of wires of each layers. The lattice, when observed normal with respect to a wall of the implantable endoluminal prosthesis, defines polygonal openings.

17 Claims, 15 Drawing Sheets

(51) Int. Cl.
*A61L 27/06* (2006.01)
*A61L 27/28* (2006.01)
*A61F 2/06* (2013.01)

(52) U.S. Cl.
CPC ......... *A61L 27/28* (2013.01); *A61F 2002/016* (2013.01); *A61F 2002/018* (2013.01); *A61F 2002/065* (2013.01); *A61F 2210/0014* (2013.01); *A61F 2210/0076* (2013.01); *A61F 2230/0006* (2013.01); *A61F 2230/0069* (2013.01); *A61F 2230/0082* (2013.01); *A61F 2250/0017* (2013.01); *A61F 2250/0023* (2013.01)

(58) Field of Classification Search
CPC ...... A61F 2/885; A61F 2/90; A61F 2002/016; A61F 2002/061; A61F 2002/065; A61F 2002/067; A61F 2002/068; A61F 2002/072; A61F 2002/075; A61F 2002/077; A61F 2/011; A61F 2/012; A61B 17/11; A61B 2017/1103; A61B 2017/1107; A61B 2017/1132; A61B 2017/1135; A61B 2017/1139
See application file for complete search history.

(56) References Cited

U.S. PATENT DOCUMENTS

| | | | | |
|---|---|---|---|---|
| 2001/0004707 | A1* | 6/2001 | Dereume | A61F 2/07 623/1.16 |
| 2003/0100940 | A1* | 5/2003 | Yodfat | A61F 2/01 623/1.15 |
| 2003/0125801 | A1 | 7/2003 | Yodfat et al. | |
| 2004/0024416 | A1* | 2/2004 | Yodfat | A61F 2/01 606/200 |
| 2005/0010281 | A1* | 1/2005 | Yodfat | A61F 2/07 623/1.39 |
| 2006/0015138 | A1 | 1/2006 | Gertner | |
| 2006/0195183 | A1* | 8/2006 | Navia | A61F 2/2409 623/2.18 |
| 2007/0162104 | A1* | 7/2007 | Frid | A61F 2/856 623/1.15 |
| 2007/0208373 | A1 | 9/2007 | Zaver et al. | |
| 2009/0270974 | A1 | 10/2009 | Berez et al. | |
| 2014/0348860 | A1 | 11/2014 | Barbick et al. | |

FOREIGN PATENT DOCUMENTS

| | | |
|---|---|---|
| WO | 03006097 A1 | 1/2003 |
| WO | 2013082555 A1 | 6/2013 |
| WO | 2013132478 A2 | 9/2013 |

OTHER PUBLICATIONS

Sievert et al., "A Novel Carotid Device for Embolic Diversion: Lessons Learned from a "First in Man" Trial in Patients with Atrial Fibrillation", Cardiovasc. Intervent. Radiol., Apr. 2012 (Published online: Oct. 19, 2011), vol. 35, issue 2, pp. 406-412, Copyright Springer Science+Business Media, LLC and the Cardiovascular and Interventional Radiological Society of Europe (CIRSE) (2011); DOI: 10.1007/s00270-011-0290-z.

International Search Report dated Dec. 9, 2016 for International Application No. PCT/EP2016/071311 filed Sep. 9, 2016.

* cited by examiner

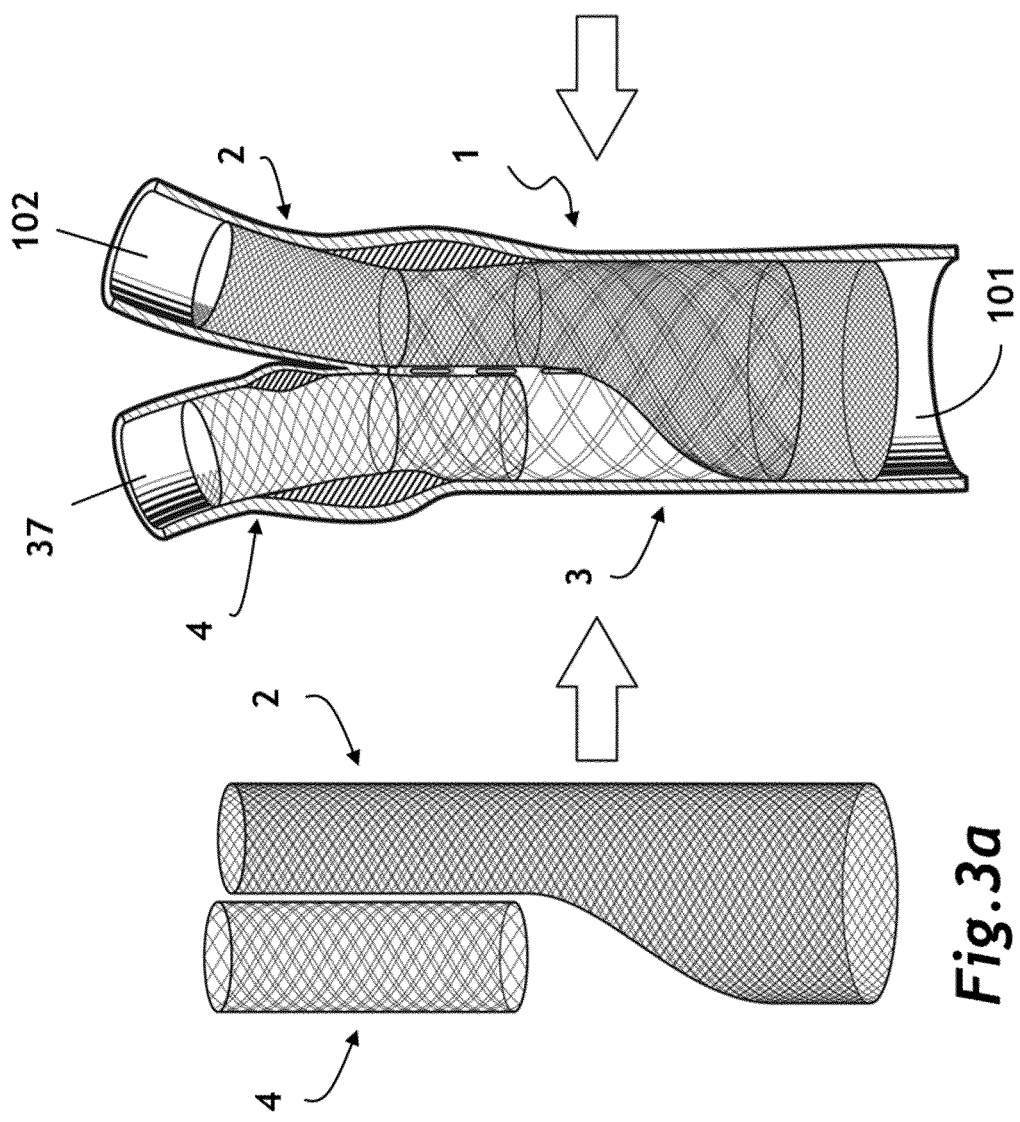

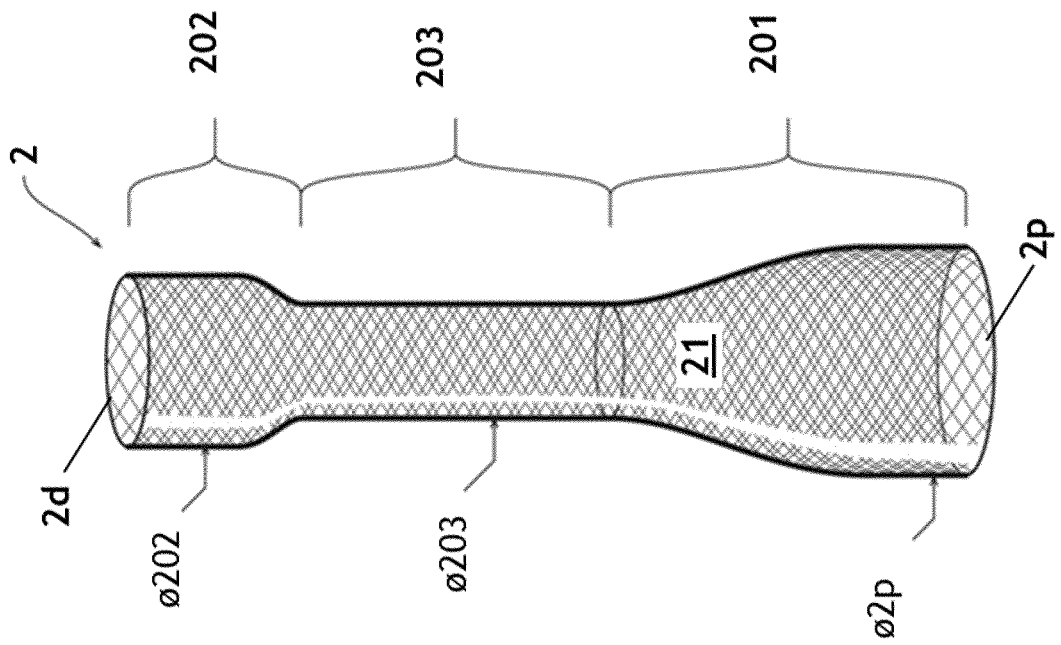
Fig. 5 (INV)
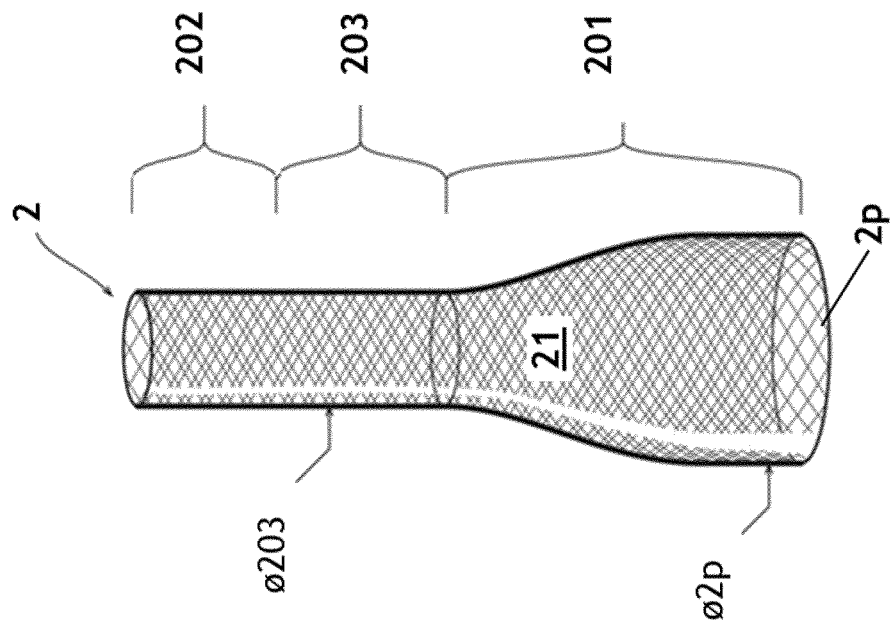
Fig. 4 (INV)

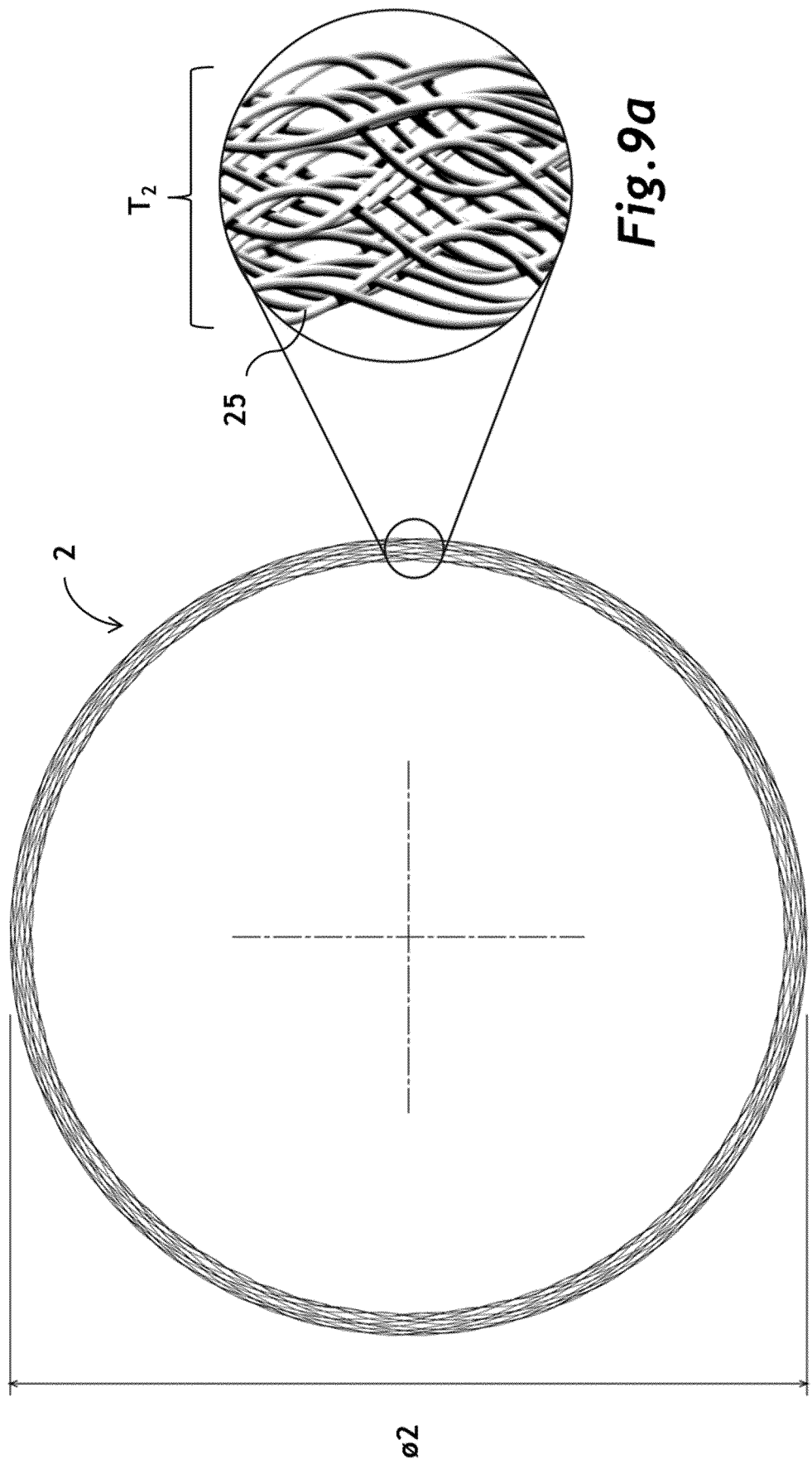

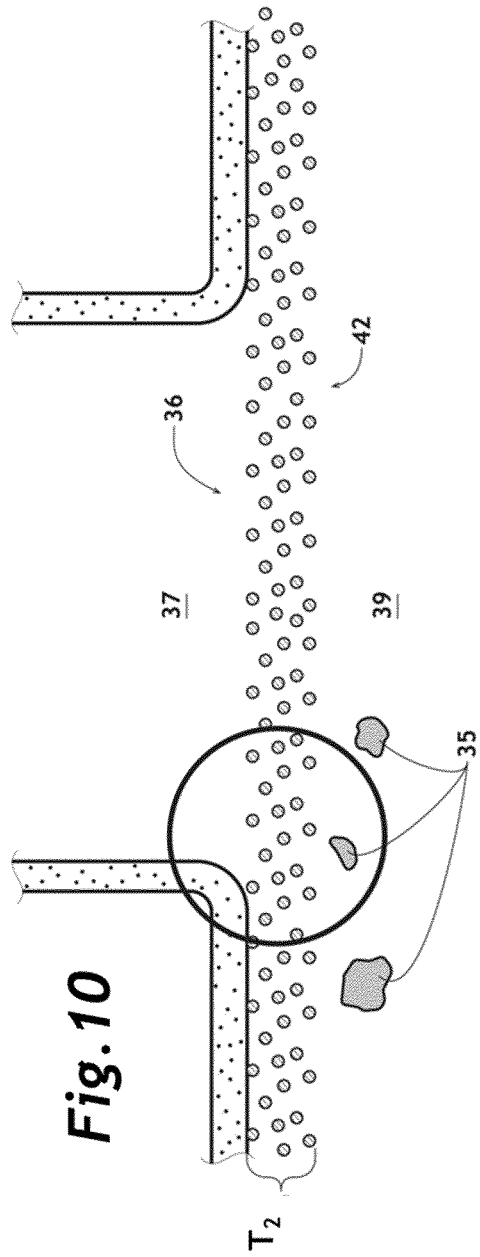
Fig.10
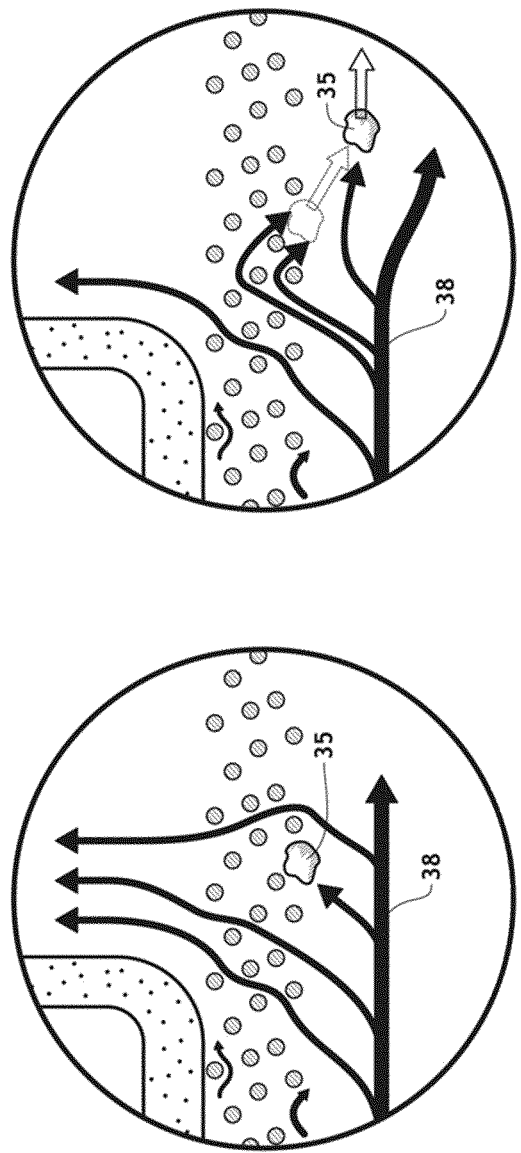
Fig.10a
Fig.10b

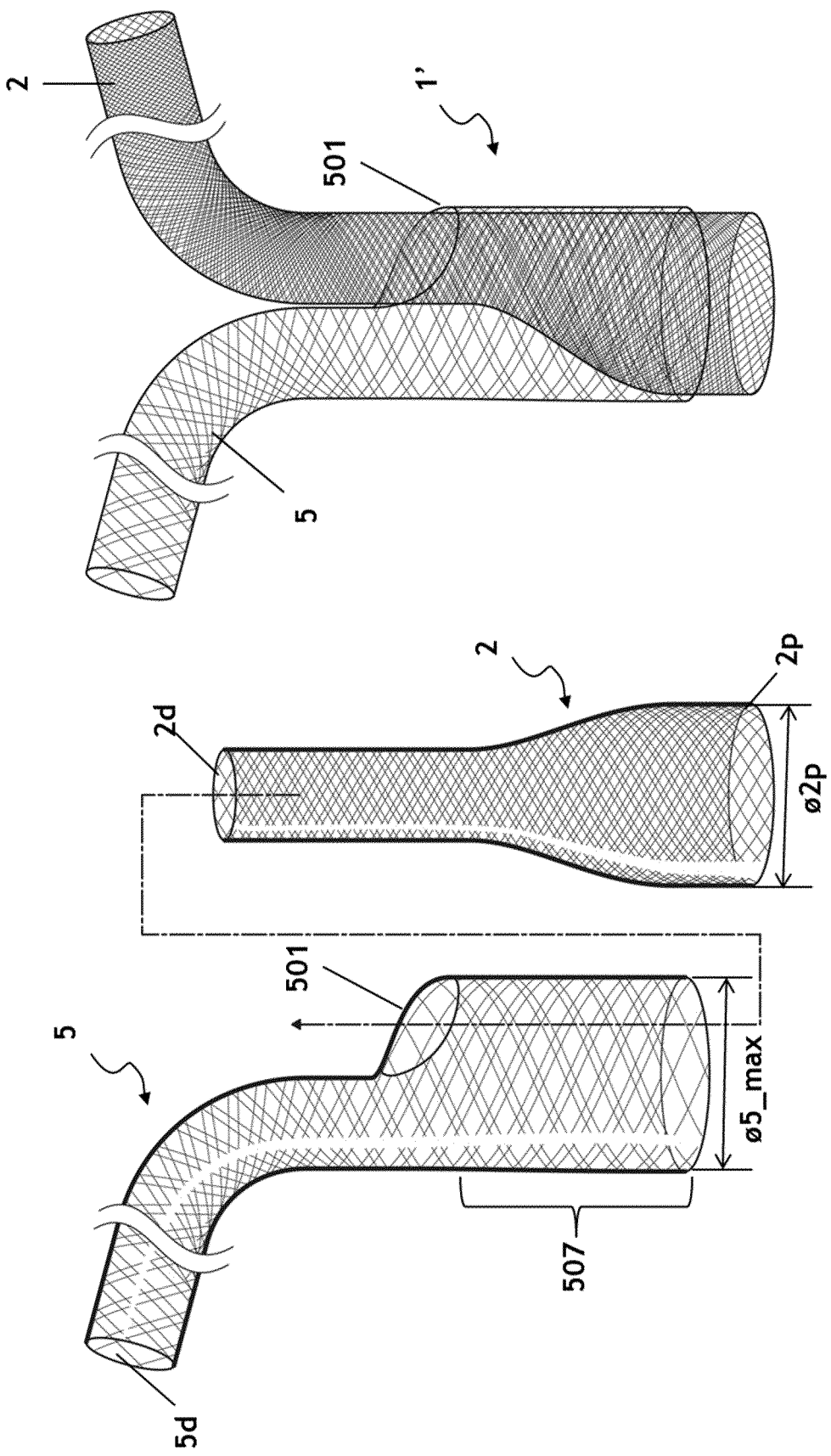

BIFURCATED 3D FILTER ASSEMBLY FOR PREVENTION OF STROKE

TECHNICAL FIELD

The present invention relates to implantable endoluminal prostheses for preventing clots migration to avoid ischemic stroke. More particularly, the present invention is related to a 3D filter-stent assembly that is placed permanently at the bifurcation zone of the common carotid artery (CCA), where the latter splits into the external carotid artery (ECA) and the internal carotid artery (ICA), so as to prevent embolic material and blood clots from entering into the ICA, which carries blood to the brain. The present invention also relates to methods for manufacturing such implantable endoluminal prostheses.

BACKGROUND OF THE INVENTION

Strokes constitute an abrupt impairment of brain function caused by interruption of oxygen supply to the brain. Sudden occlusion of an artery supplying blood to the brain by embolic materials causes ischemic stroke. There are two main types of sources of embolic materials; materials detached from atherosclerosis plaques of the wall of the aorta and coagulated blood clots escaping from the heart. Ischemia can also occur in other organs such as the kidneys and the liver.

About 20% of ischemic strokes are caused by cardioembolism. They are primarily caused by embolism of thrombotic material forming on the arterial or ventricular wall, or the left heart valves. These are expected when cardiac arrhythmia or structural abnormalities are present. The most common cases of cardioembolic strokes are nonrheumatic arterial fibrillation (AF), prosthetic valves, rheumatic heart disease (RHD), ischemic cardiomyopathy, congestive heart failure, myocardial infarction, post-operatory state and protruding aortic arch atheroma.

Anticoagulants are a class of drugs commonly used to prevent the blood from forming dangerous clots that could lead to a stroke. Anticoagulants are frequently used in patients who are already at high risk for stroke.

Warfarin, for example, belongs to a class of drugs called vitamin K antagonists (VKAs) meaning that they interfere with the normal action of vitamin K, which is involved in the blood clotting process. Warfarin, the predominant anticoagulant in clinical use, reduces AF-related stroke by 64%, although this reduction is accompanied by an inherent risk of hemorrhagic complications, among which cerebral haemorrhages are especially serious. Accordingly, for up to 40% of patients with AF an anticoagulation therapy is contraindicated. The VKA has further a narrow therapeutic window and requires frequent laboratory monitoring and subsequent dose adjustments.

Prior art filter devices have up to now not been completely successful. U.S. Pat. Nos. 6,673,089 and 6,740,112 disclose a "self-expandable single-layer wire braided mesh" 106 designed to be positioned at the bifurcation zone of the common carotid artery (CCA, 101) to the external carotid artery (ECA, 102). Theoretically, this braided mesh is deemed to deviate emboli debris to the ECA 102 (which brings the blood toward the face) and avoid carrying them to the brain via the internal carotid artery (ICA, 37). The rerouting efficacy of emboli debris into the ECA 102 was assessed clinically by Sievert et al. in Cardiovas Intervent Radiol (2012) 35:406-412, "A novel carotid device for embolic diversion" in three patients during 6 to 14 months follow-ups and high risk of filter occlusion is observed in front of the ICA orifice 36. This conventional filter device 106 is faced to another problem when, as shown in FIG. 1, the patient suffers from a carotid stenosis caused by atherosclerosis 105 at the very beginning of the ICA 37 as shown in FIG. 1. In that case, even if the filter device 106 would succeed in preventing the embolic materials 35 from entering into the ICA 37, it could not prevent the atherosclerosis plaques 105 consisting of the carotid stenosis debris of the plaque 105 from travelling toward the brain once this plaque 105 begins to break up.

Combination of a conventional filter device 106 and a conventional stent 107 as shown in FIG. 2 might be used for treating the carotid stenosis at the bifurcation zone of the CCA 101 while preventing stroke, but this solution is far from ideal. Since an adequate fastening zone is missing at the beginning of the conventional stent 107, undesired migration of the stent may occur after implantation, causing a lack of sealing. Furthermore, a gap may occur and grows between the filter device 106 and the stent 107. This, in turn, will produce an undesired turbulent flow, resulting in lack of sealing and creation of an accelerated formation of aneurysm.

Accordingly, there is a need for new implantable permanent filters able to use for the patient having carotid stenosis for prevention of stroke.

SUMMARY OF THE INVENTION

An object of the invention is to provide a prosthesis for preventing embolic materials from entering into ICA while minimizing the risk of filter occlusion, particularly for a patient suffering from a carotid stenosis caused by atherosclerosis at the very beginning of the ICA.

Another object of the invention is to provide a prosthesis assembly for treatment of carotid stenosis involving bifurcation zone of the CCA, while maintaining the blood flowing downstream free of small plaque debris ripped off from a wall of the CCA bifurcation zone or from the very beginning of the ICA as well as embolic materials flowing from the heart or the aorta.

The subject of the invention is an implantable permanent filter assembly suitable for deployment in a multifurcated vessel such as bifurcated vessel comprising a main vessel and at least two branches. This assembly comprises a filtering sleeve formed of a self-expandable braided framework able to expand from a radially compressed state in a delivery configuration to a radially expanded state. The filtering sleeve extends along an axis and defines a lumen devoid of impermeable layer, having a distal end configured to extend toward the branches of the bifurcated vessel and a proximal end configured to extend toward away from the branches of the bifurcated vessel. The braided framework comprises a plurality of layers of wires made of biocompatible material, each layer forming a mesh, the meshes forming a lattice with a plurality of wires of each layer. The lattice, when observed normal with respect to a wall of the filter sleeve, defines polygonal openings, the diameter ($\varnothing_{25}$) of wire being at least 20 μm and at most 100 μm. The filtering sleeve includes a proximal region for implantation in the CCA, a distal region for implantation in the ECS and a neck region extending to a proximal and a distal regions and preferably having a constant diameter. The proximal region of the filtering sleeve has a diameter enlarging toward the proximal end. The diameter at the proximal end is between 1.5 and 3.5 times larger than the diameter of the neck portion in the fully expanded state; the braided framework consist of at least 90, preferably at least 100, more preferably at least 120, even more preferably at least 160 wires; the ratio ($T_2/\o_{25}$) of the thickness ($T_2$) of a wall of the filtering sleeve to the diameter ($\o_{25}$) of the wires is at least 3, preferably at least 3.5, more preferably at least 4.0, even more preferably at least 4.5; in a fully expanded state, the surface coverage ratio (SCR) of said braided framework is more than 40% and less than 90%, preferable more than 50%. A mean diameter ($\o_{27}$) of the inscribed circle of each polygonal opening of the proximal portion is at least 50 μm and at most 200 μm in fully expanded state. The braided framework is formed of interlocked multilayer braiding.

The implantable filter assembly further comprises an expandable main body component and an extension sleeve. The main body component is able to expand from a radially compressed state in a delivery configuration to a radially expanded state. This main body component comprises towards its distal end, a concaved portion comprising a double-barrelled portion. The diameter of the extension sleeve is smaller than the maximum diameter defined as the largest diameter of the main body component so as to fit the bifurcated vascular morphology. The diameter at the proximal end of the filtering sleeve is equal to or greater than the maximum diameter of the main body component so that a portion of the CCA wall will be well sealed by the proximal part of the filtering sleeve in order to maintain the blood flowing downstream free from small plaque debris that ripped off from a wall of the CAA bifurcation zone or from the very beginning of the ICA.

The middle lines of the concaved portion are concaved along the longitudinal axis of the main body component and define two opposing ridges extending toward the interior of the concaved portion. Each ridge partially contacts the other ridge, the two opposing ridges thus defining two lumens in the double-barrelled portion. Both lumens extend along an axis, the axes of the two lumens defining a central plane (CP) which also comprises the axis of the main body component.

As a preferable embodiment, at a proximal end of said main body component, the main body component preferably comprises a sealing portion having a lumen of cylindrical form with a circular cross-section and a constant diameter which is greater than the diameters of the cylinder body portion and the concaved portion in expanded state. A proximal part of said filtering sleeve has such dimensions that the filtering sleeve is able to be deployed inside the sealing portion of the main body component. The neck region of the filtering sleeve has such dimensions that the filtering sleeve is able to be deployed inside one of the two lumens of the double-barrelled portion of the concaved portion The sealing portion reduces a risk of migration of the main body component during delivering the filter sleeve through the lumen of the deployed main body component.

The main body component is advantageously formed of a braiding with a plurality of filaments and devoid of any cover layer, having a multilayered configuration, preferably formed of an interlocked multilayer braiding so that the implantable permanent filter assembly prevents damage of the artery by eliminating an undesired turbulent flow in a gap created between the filter assembly and the artery wall.

Advantageously the extension sleeve is formed of a braiding with a plurality of filaments and devoid of any cover layer, preferably formed of an interlocked multilayer braiding.

According to advantageous embodiments, the braided framework and/or the main body component and/or the lumen extension are self-expandable.

As another embodiment, the wires of braided framework are covered with phosphonate containing a hydrocarbon chain comprising 3 to 16 carbon atoms as a linier chain. The phosphorus atom of the phosphonate bonds to the hydrocarbon chain at the alpha-position, said hydrocarbon chain being further functionalized at its terminal position by a carboxylic group, a phosphonic group or a hydroxyl group. The phosphonate is covalently and directly bonded to the external surface of the wire and covering at least 50% of the external surface of the wire as monolayer and as an outermost layer.

As another embodiment, the wires are covered with a gem-bisphosphonate so that at least one phosphonate moiety is covalently and directly bonded to the external surface of the wire. The bisphosphonate covers at least 50% of the external surface of the wires as monolayer and as an outermost layer. Advantageously, the gem-bisphosphonate is selected from a group consisting of etidronic acid, alendronic acid, clodronic acid, pamidronic acid, tiludronic acid, risedronic acid or a derivative thereof.

BRIEF DESCRIPTION OF THE DRAWINGS

Other particularities and advantages of the invention will appear from the description hereafter of a series of embodiments, taken as examples, reference being made to the appended drawings, wherein:

FIG. 3 is a cutaway view of an implantable permanent filter assembly according to the invention;

FIGS. 3a and 3b are perspective views of parts of the prosthesis shown at FIG. 3;

FIG. 4 is a lateral view of a filtering sleeve of the assembly of the invention;

FIG. 5 is a lateral view of another embodiment of the filtering sleeve;

FIG. 9 is a cross-view of a filtering sleeve;

FIG. 9a is a detailed view of an interlocked multiple-layer configuration of the braided framework;

FIGS. 10, 10a and 10b, are sketches showing in details embolic materials flowing toward an orifice of the ICA;

FIGS. 19 and 20 show another embodiment of prosthesis before and after assembled respectively according to the present invention;

DETAILED DESCRIPTION OF THE INVENTION

Figure 2:
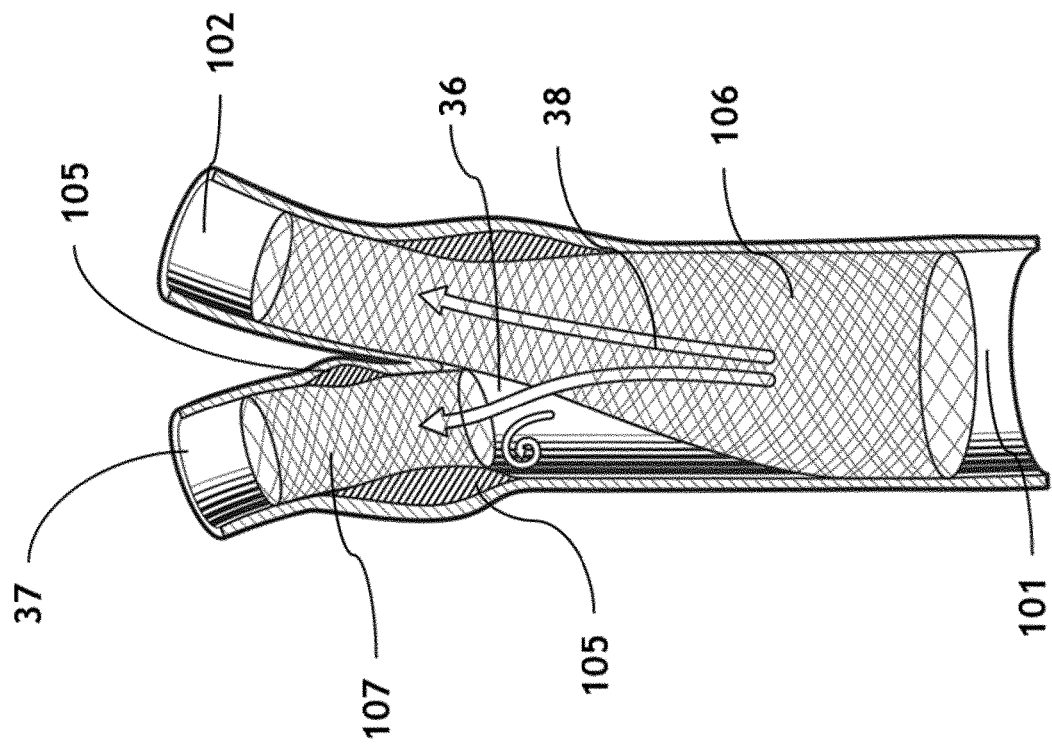
FIG. 2 is a sketch of a prior art solution.

As used herein, the term "implantable" refers to an ability of a medical device to be positioned at a location within a body vessel. Implantable medical device can be configured for transient placement within a body vessel during a medical intervention (e.g., seconds, minutes, hours), or to remain in a body vessel permanently.

The terms "endoluminal" or "transluminal" prosthesis refers to a device adapted for placement in a curved or straight body vessel by procedures wherein the prosthesis is advanced within and through the lumen of a body vessel from a remote location to a target site within the body vessel. In vascular procedures, a medical device can typically be introduced "endovascularly" using a catheter over a wire guide under fluoroscopic guidance. The catheters and wire guides may be introduced through conventional access sites in to the vascular system.

The term "catheter" refers to a tube that is inserted into a blood vessel to access the target site. In the present description, a "catheter" will designate either a catheter per se, or a catheter with its accessories, meaning needle, guide wire, introducer sheath and other common suitable medical devices known by the man skilled in the art.

The term "preventing" includes rejecting or inhibiting the embolic material from entering a specified blood vessel, such as a branch blood vessel.

To avoid any confusion, in the description herein below, the terms of "opening", "pore" and "window" have their ordinary meaning and are also used interchangeably to refer to an open channel or passageway from one face or surface of a medical device to its other face or surface. Similarly, the terms of "inlet", "junction" and "orifice" refer to an area in vasculature where at least one branch blood vessel diverges from the main blood vessel.

The term "endothelialisation" refers to a cellular process resulting in ingrowth of the endothelial cells onto a device.

The term "permanent" refers to a medical device which may be placed in a blood vessel and will remain in the blood vessel for a long period of time (e.g. months, years) and possibly for the remainder of the patient's life.

The terms "embolus", "embolic material" and "filtrate" refer to a clot or other biologic material which has been brought to its site of lodgement by the blood flow. The obstructing material is most often a blood clot (i.e., thrombus), but may be a fat globule (due to atherosclerosis), piece of tissue or clump of bacteria.

FIG. 3 displays a preferred embodiment of an implantable permanent filter assembly 1 according to the present invention, which comprises a filter sleeve 2, a main body component 3 and an extension sleeve 4. The assembly 1 has a distal end configured to extend toward the branches of the bifurcated vessel and a proximal end configured to extend toward away from the branches of the bifurcated vessel and extending along an axis. The assembly 1 is designed to be "permanently" implanted in a vessel lumen.

The filter sleeve 2 consists of a braided framework 20 which defines a cylindrical lumen 21, and is formed of a self-expandable braiding able to expand from a radially compressed state in a delivery configuration to a radially expanded state. The filter sleeve 2 is devoid of any impermeable membrane. As shown in FIG. 4, the filtering sleeve 2 includes a proximal region 201 for implantation in the CCA 101, a distal region 202 for implantation in the ECA 102 and a neck region 203 extending to the proximal and the distal regions and preferably having a constant diameter. The proximal region 201 of filtering sleeve 2 has a diameter enlarging toward its proximal end 2p. The diameter ($\varnothing_{2p}$) at the proximal end 2p is larger than a diameter ($\varnothing_{203}$) of the neck portion 203 in the fully expanded state, preferably $\varnothing_{2p}$ is between 1.5 and 3.5 times larger than $\varnothing_{203}$. The distal region 202 has advantageously a larger diameter than the one of the neck region 203 as shown on the embodiment of FIG. 5.

Referring to FIGS. 6, 7a-7c and 8a-8c, the braided framework 20 of the filter sleeve 2 comprises a plurality of layers 22, 23, 24 of wires 25 made of biocompatible material. The wires 25 have a diameter ($\varnothing_{25}$) of at least 20 µm and at most 100 µm, preferably at least 30 µm and at most 75 µm, more preferably at most 100 µm. Each layer of the braided framework 20 forms a mesh. When observed normal with respect to a wall of the filter sleeve 2, meshes of the braided frame 20 form a lattices with a plurality of level of wires 25. Preferably, the meshes are interlocked to each other so as to form an interlocked multi-layer structure having a three dimensional structure. The term "interlocked multi-layer" refers to a framework comprising multiple layers, 22, 23, 24, whose plies are not distinct at the time of braiding, for example a given number of wires of the plies of the first layer 22 being interlocked with the plies of the second layer 23 and/or other layers 24. Said interlocked multi-layer, for example, can be formed by using the braiding machine described in EP1248372. The braided framework 20 of the filtering sleeve 2 is made of at least 90 and at most 512 of wires 25, preferably at least 100, more preferably at least 120, even more preferably at least 160 and at most 320 of wires 25.

The braided framework 20 is configured to take a compressed shape having a relatively small and relatively uniform diameter when disposed within a delivery system, such as a catheter (i.e., "in compressed state"), and to take spontaneously a deployed shape having radially expanded diameter within the delivered location such as a body lumen (i.e., "in deployed state") as shown in FIG. 3. As used herein the term of "expanded shape" or "expanded state" refers to respectively a shape or state resulting from the self-expanding properties of a self-spring-back object (e.g., braided framework 20) when it is expanded without any outer compression force (i.e., non-constricted state) as shown in FIG. 4. Beside these definitions, the term "nominal diameter" designates the diameter of the stent-filter when placed in the targeted a vessel. Generally, the nominal diameter ($\varnothing_{nor}$) of a self-expandable device designed to be placed permanently inside a body lumen is 10 to 25% smaller than the external diameter of said device when deployed without external compression force ($\varnothing_{exp}$). For example, since an inner diameter ($\varnothing_{106}$) of the CCA 106 is generally between 5.0 mm and 11.0 mm, the proximal region 201 of filtering sleeve 2 according to the present invention is accordingly designed and/or manufactured to have a diameter ($\varnothing_{201\_exp}$) between 5.5 mm and 12 mm in expanded state. Variations of the diameter of the filtering sleeve 2 influence, in turn, its length. The length ($L_{2\_dep}$) of the filtering sleeve 2 according to the invention in deployed state is thus greater than its length ($L_{2\_exp}$) in expanded state. The length-related compression ratio (LCR) of the filtering sleeve 2 can be defined by the relation:

$$LCR=(L_{2\_dep}-L_{2\_exp})/L_{2\_exp}$$

When the filtering sleeve 2 is deployed in a curved lumen, its length ($L_{2\_dep}$) in deployed state is measured along the midpoint of the curve.

Figure 6:
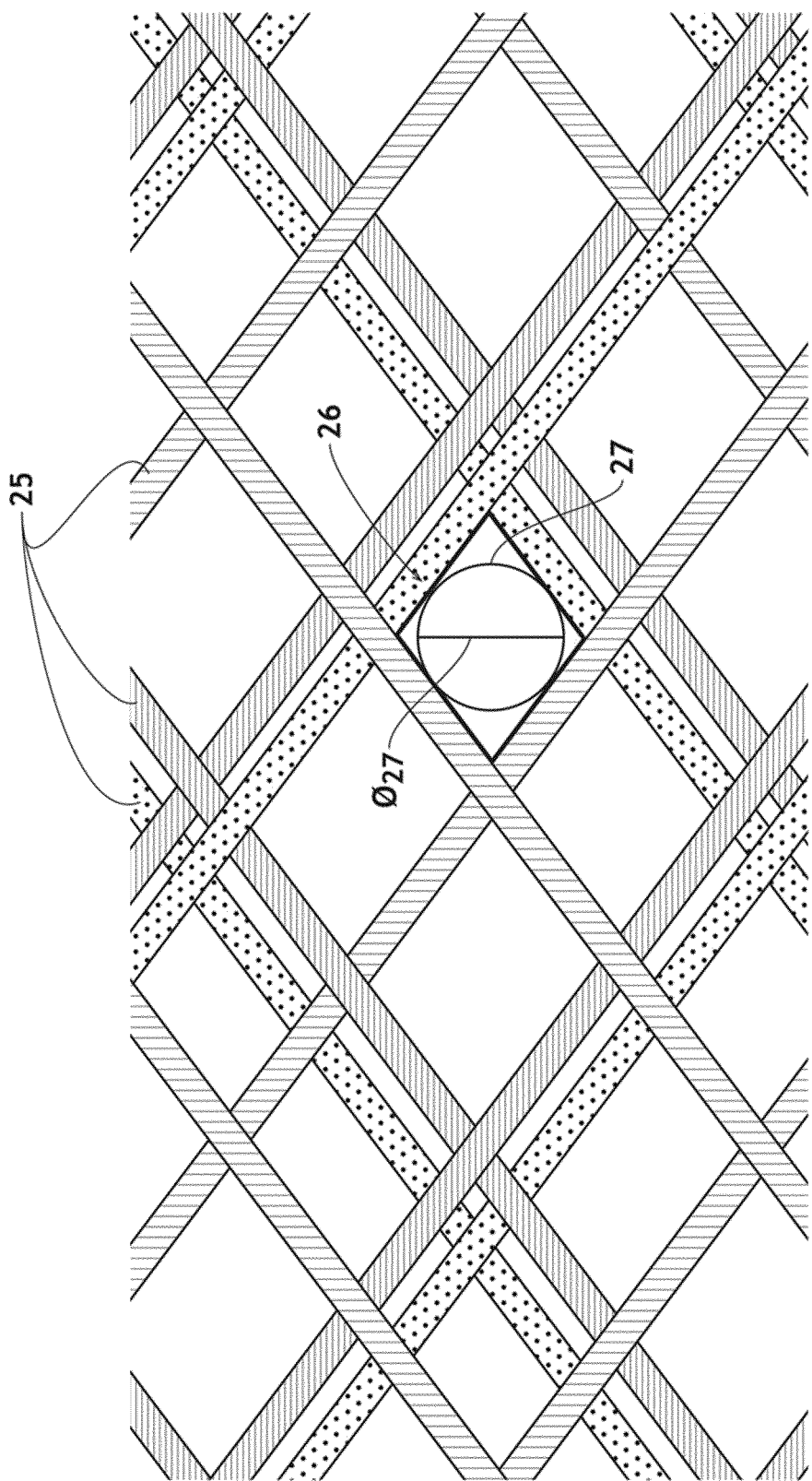
FIG. 6 is a detailed view of the braided framework observed normal with respect to a wall of the filter sleeve.
Figure 7A:
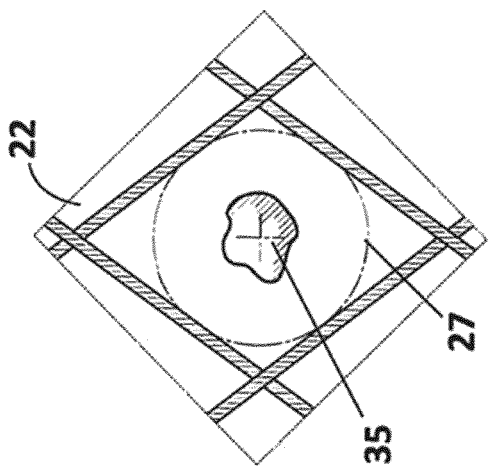
FIGS. 7a-7c and 8a-8c schematically describe how the filtering sleeve deviates or blocks an embolic material trying to get through the wall.
Figure 7B:
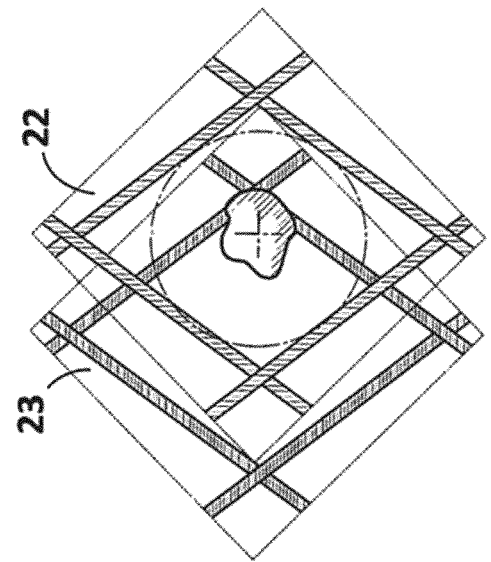
Figure 7C:
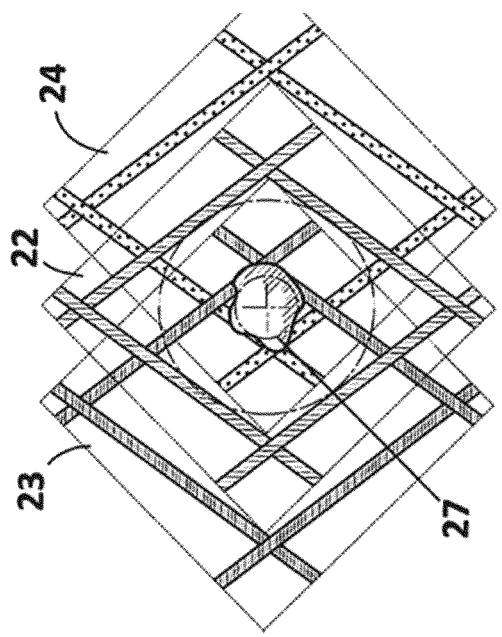
Figure 8A:
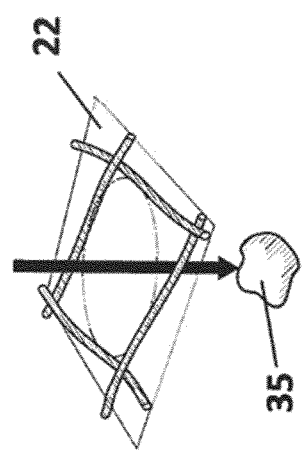
Figure 8B:
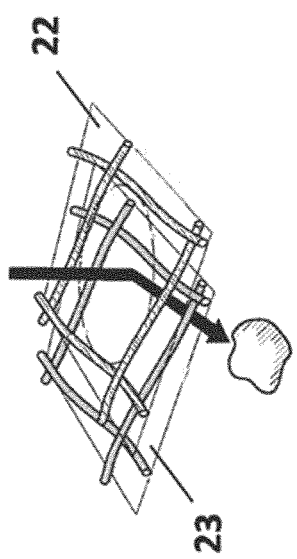
Figure 8C:
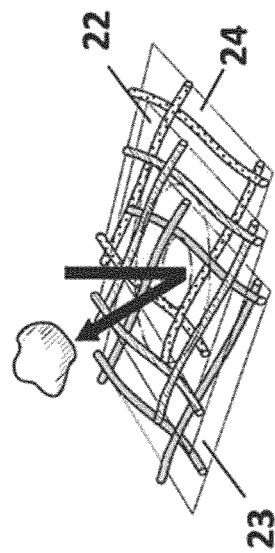

The lattice of the braided framework defines opening 26 having a polygonal shape defined by roughly straight sides (in reality, wire segments). The polygonal shape is preferably a quadrangle, more preferably a parallelogram. "Parallelogram" means a simple quadrilateral defined by two pairs of parallel segments; the facing sides of a parallelogram are of equal length; the opposite angles of a parallelogram are of equal measure; and the diagonals bisect each other. Parallelograms include squares, rectangles, and lozenges. As used herein, "inscribed circle" 27 refers to the largest circle that can be drawn inside the polygonal opening 26 and tangent to at least three of its sides (i.e. wires segments 25) as depicted in FIG. 6.

The size of the inscribed circle 27 directly reflects the efficacy to deflect embolic material 35, particularly micro-embolus that would have flown into the ICA 37, to the ECA 102. "Micro-embolus" refers to an embolus of microscopic size, for example, a tiny blood clot or a little clump of bacteria. Micro-emboli are either gaseous or solid embolic material. The gaseous micro-emboli can originate from mechanically induced cavitation created by a prosthetic heart valve. They have an approximate diameter of 4 µm and cause normally no deleterious effect on the brain. In contrast, solid microemboli are much bigger than gaseous micoremboli, having an approximate diameter of 100 µm. The larger size of solid microemboli compared to the size of capillaries (diameter 7-10 µm) can cause blockage of micro circulation. In J. Endovasc. Ther., 2009; 16; 161-167, "Reduction of cerebral embolixation in carotid angioplasty: An in-vitro experiment comparing 2 cerebral protection devices" published by Charalambous et. al., either gaseous or small emboli having diameter less than 200 µm cause only clinically unperceived cerebral ischemia.

Therefore, in order to reroute embolic material having more than 200 µm, a mean diameter ($\emptyset_{27}$) of inscribed circle 27 (IC) of polygonal openings 26 of the proximal region 201 is preferably at most 200 µm, preferably at most 150 µm, more preferably at most 100 µm. At the same time, since the openings should be large enough to let the blood components get through the wall of the filtering sleeve 2 and keep adequate perfusion, the mean IC diameter should be at least 50 µm, preferably at least 75 µm. The mean diameter ($\emptyset_{27}$) of inscribed circle 27 (IC) of polygonal openings 26 means the value found by adding all the diameters of inscribed circle 27 and dividing the total by the number of openings 26. The polygonal openings 26 can be measured with stereo-microscopy. High-resolution digital images were taken of each segment of the filtering sleeve on a mandrel which is programmed to rotate by increments of 15° from the starting 0° position to 360°. A stereo-microscopy was positioned to be nominal to a wall of the filtering sleeve. The 24 pictures were then combined to each other, and examined with image analysis software. The mean diameter ($\emptyset_{27}$) of IC can be measured by randomly picking up five square portions from the combined picture as comprising at least 10 openings and by averaging diameters of ICs of these openings. The combined picture can also be used to calculate surface coverage ratio (SCR) of the braided framework as mentioned below, by randomly picking up five square portions therefrom as comprising at least 10 openings.

One of advantages of the filter assembly 1 according to the present invention is that the filtering sleeve 2 having a higher value of $T_2/\emptyset_{25}$ can prevent effectively an embolic material 35 from flowing across its wall as shown in FIGS. 7a-7c, 8a-8c and 9a in comparison with a conventional filter having less than 2.0 of $T_2/\emptyset_{25}$. The ratio ($T_2/\emptyset_{25}$) of the wall thickness ($T_2$) of the endoluminal prosthesis to the wire diameter ($\emptyset_{25}$) being at least 2.0 characterizes a braided framework having a three dimensional structure comprising more than a single layer of mesh. The greater the ratio $T_2/\emptyset_{25}$, the more layers the braided framework 20 will comprise. Each wire forming multiple-layers aligned substantially parallel in the wall, as shown in FIG. 9, has a chance to deviate or block an embolic material 35 trying to go through the wall of the filtering sleeve 2, as schematically explained in FIGS. 7a-7c and 8a-8c. The present structure can thus increase the emboli rerouting efficacy. The ratio $T_2/\emptyset_{25}$ of the filtering sleeve 2 should therefore reach at least 3, preferably at least 3.5, more preferably at least 4.0, even more preferably at least 4.5.

Furthermore, an interlocked multiple-layer configuration affording a $T_2/\emptyset_{25}$ value higher than 2.5 provides an important technical property: when it is deployed in a curved lumen having Angle α between 10° and 48°, the mean inscribed circle diameter ($\emptyset_{27}$) of openings stay between 50 µm and 250 µm at the outer side of the curve 29. Since the orifice 36 of the ICA 37 is located at the outer side of the curve, it is most important to set an optimal opening size at the outer side when deployed in the bifurcation zone of the CCA 101 in order to improve filtering efficacy. Wires of the present interlocked multiple-layer configuration shift to have a regular distance between adjacent parallel wires in a curved, deployed state, resulting in that the mean inscribe diameter ($\emptyset_{27}$) stays almost the same as the one in straight configuration.

The surface coverage ratio (SCR) of the braided framework 20 is defined by the relation:

$$SCR=S_w/S_t$$

wherein: "$S_w$" is the actual surface covered by wires 25 composing the braided framework 20, and "$S_t$" is the total surface area of the wall of the braided framework 20. In a fully expanded state, SCR of the filtering sleeve 2 is more than 40%, preferably at least 50%, even more preferably at least 55%, still even more preferably at least 60%. When deployed in a C-curved lumen 30 having a nominal diameter of the filtering sleeve 2 with Angle α being between 10° and 48°, the braided framework 20 with at least 3.0 of the ratio of $T_2/\emptyset_{25}$ (preferably 3.5, more preferably at least 4.0, even more preferably at least 4.5) can provide almost the same surface coverage ratio (SCR) along its outer curve 29 as the one in its straight configuration, i.e. more than 40%. It is another advantage of the present invention, resulting in improvement of emboli rerouting efficacy.

Filtering devices known in the art often become clogged and need to be cleaned or even replaced. An endoluminal prosthesis designed to be positioned permanently in a blood vessel should have an inherent ability to clean itself or be cleaned by endogenous forces or effect so as to avoid periodic cleaning by a physician or removal of the device from the blood vessel.

The present filtering sleeve 2 having a sufficient wall thickness ($T_2$) with respect to the size of the opening 26, (i.e.

the inscribed circle diameter ($\varnothing_{27}$)), imparts high self-cleaning properties in comparison with conventional filter devices. As shown in FIGS. 10,10*a* and 10*b*, some embolic materials 35 flowing about an orifice 36 of the ICA 37 are temporally pushed against an interior surface 42 of the filtering sleeve 2 in front of the ICA 37 as a result of blood inflow through a wall thereof during the ventricular systole and the relaxation phase of the cardiac cycle. Thanks to the sufficient wall thickness $T_2$ of the braided framework 26, these embolic materials 35 are kept trapped on the interior surface 42 instead of passing through the wall, and are then flushed away and back into the blood stream 38 during the atria systole, as a result of the flushing expelling force. The term "flushing expelling force" refers to a discovered inherent property of the filtering sleeve 2. Specifically, it is the force that is imparted to the embolic material 35 by the flowing blood 38 with which it comes in contact.

Studies and experiments carried by the inventor led to surprising and unexpected conclusions. If the ratio $T_2/\varnothing_{25}$ is smaller than 2.0, as in conventional filters, the embolic material 35 is either flushed through the mesh openings and enters into the ICA 37 or accumulates till it blocks the blood flow at the orifices of the branches. The greater the ratio $T_2/\varnothing_{25}$, the greater the flushing expel force the filtering sleeve 2 will exhibit. Therefore, the present filtering sleeve 2 reduces the occlusion risk of the branches orifice covered thereby, resulting in an increase of safety in use. The ratio $T_2/\varnothing_{25}$ should be at least 2.5, preferably at least 3.0, more preferably 3.5, even more preferably 4.0, still more preferably at least 4.5, even more preferably at least 5.0, so as to improve safety of the device.

The biocompatible material preferably metallic substrate selected from a group consisting of stainless steels (e.g., 316, 316L or 304); nickel-titanium alloys including shape memory or superelastic types (e.g., nitinol, Nitinol-DFT®-Platinum); cobalt-chrome alloys (e.g., elgiloy); cobalt-chromium-nickel alloys (e.g., phynox); alloys of cobalt, nickel, chromium and molybdenum (e.g., MP35N or MP20N); cobalt-chromium-vanadium alloys; cobalt-chromium-tungsten alloys; magnesium alloys; titanium alloys (e.g., TiC, TiN); tantalum alloys (e.g., TaC, TaN); L605. Said metallic substrate is preferably selected from the group consisting of titanium, nickel-titanium alloys such as nitinol and Nitinol-DFT®-Platinum, any type of stainless steels, or a cobalt-chromium-nickel alloys such as Phynox®.

As additional surprising effect provided by the filtering sleeve 2 according to the present invention, the perfusion in the ICA is improved in accordance with the increase of $T_2/\varnothing_{25}$ value. "Perfusion" is, in physiology, the process of a body delivering blood to capillary bed in its biological tissue. The terms "hypoperfusion" and "hyperperfusion" measure the perfusion level relative to a tissue's current need to meet its metabolic needs. Since the filtering sleeve 2 according to the present invention increases the perfusion in the ICA it covers, the brain function to which the ICA carries the blood is improved.

Figure 1:
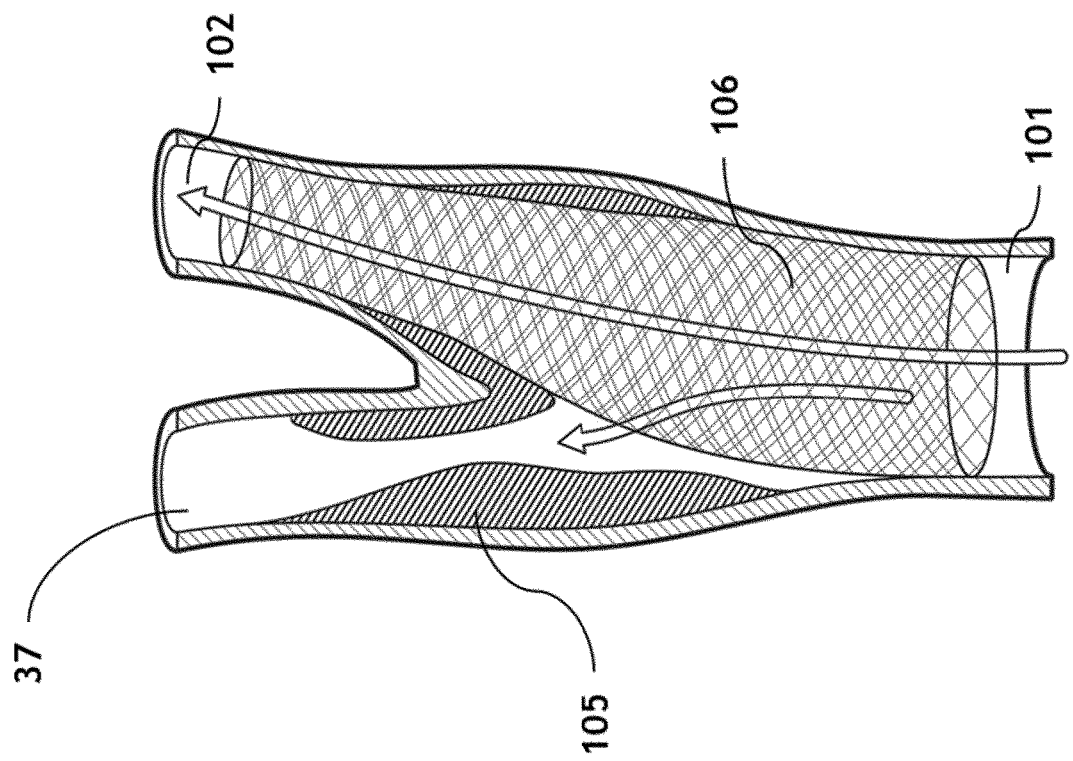
FIG. 1 is a cutaway perspective view of a bifurcation of a common human carotid with a conventional filter device.
Figure 12:
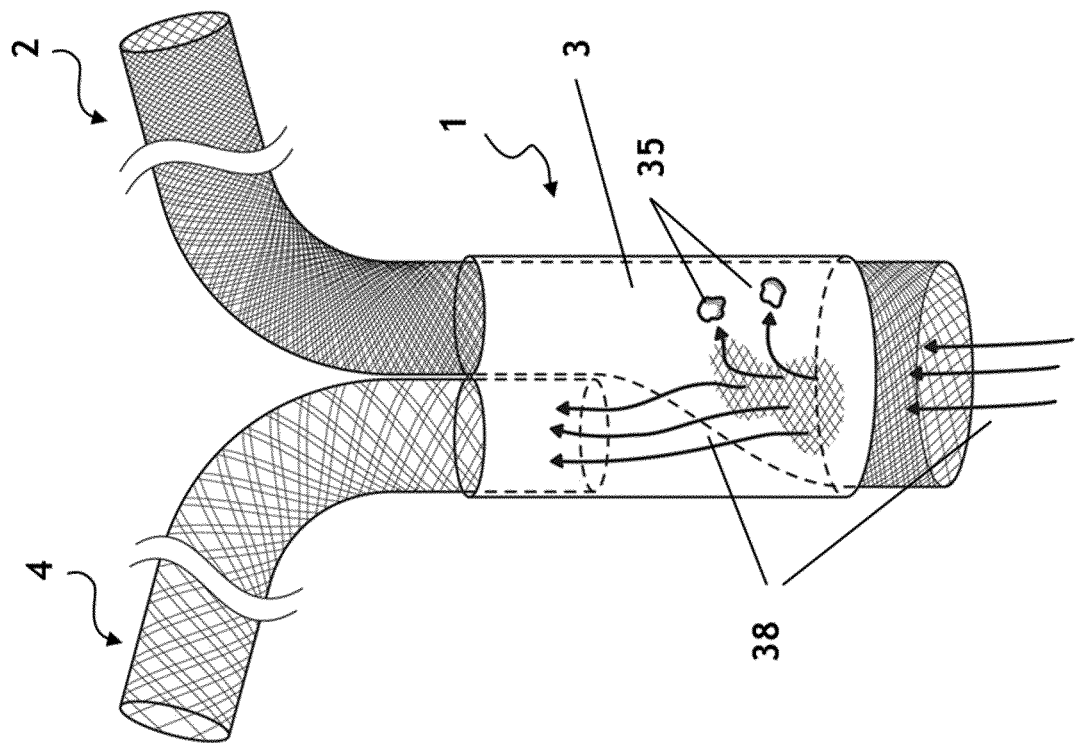
FIG. 12 is an elevation view of the parts shown at FIG. 11 inserted into a main body component.
Figure 11:
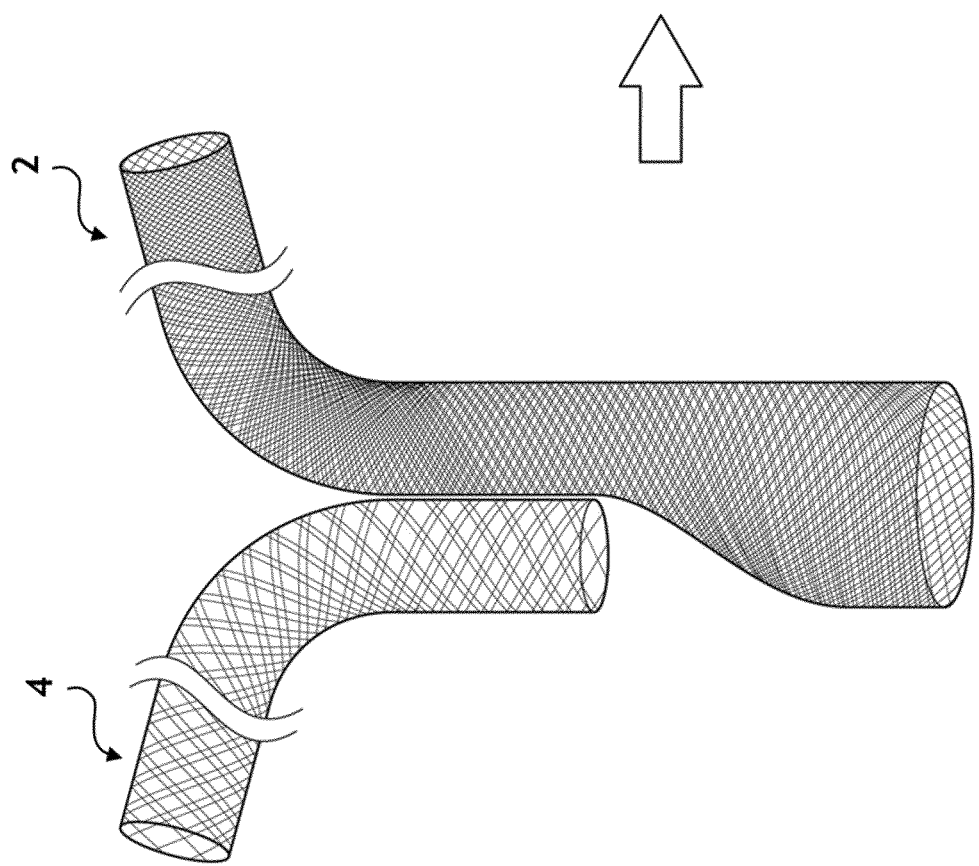
FIG. 11 is an elevation view of a filtering sleeve and a lumen extension placed side by side.

In a preferred embodiment, the main body component 3 is designed to be deployed within the bifurcation zone of the CCA prior to the extension sleeve 4 deployment and followed by the filtering sleeve 2 placement. The proximal end diameter ($\varnothing_{2p}$) of the filtering sleeve 2 is designed to be greater than or equal to the maximum diameter ($\varnothing_{3\_max}$) defined as the largest diameter of the main body component 3 in expanded state, so that a portion of the CCA wall will be well sealed by the proximal part of the filtering sleeve 2, as shown in FIG. 3. The flow of blood, possibly carrying embolic materials ripped out the heart and/or the aorta, is directed into the inner lumen 21 of the filter sleeve 2 from the proximal end 2*p* as shown in FIG. 12. Since the flow ratio between the ICA and the ECA is about 4:1, the filtering sleeve 2 lets ca. 80% of the blood flow pass through the wall of its proximal portion and enter, duly "cleaned", into the ICA while diverting the remaining 20% of the blood flow, loaded with embolic materials 35 to the ECA, as shown in FIGS. 11 and 12. As the deployed extension sleeve 4 can cover the beginning of the ICA 37, the assembly 1 is able to reduce a risk of stroke by preventing the atherosclerosis plaques consisting of the carotid stenosis shown in FIG. 1 from travelling toward the brain.

The extension sleeve 4 is preferably selected from a group consisting of stents being self-expandable, expandable by balloon angioplasty and stent-grafts suitable for Carotid artery stenting (CAS). CAS is an endovascular surgery where a stent is deployed within the lumen narrowing the carotid artery. The extension sleeve 4 preferably consists of an interlocked multilayer braided structure.

Figure 16:
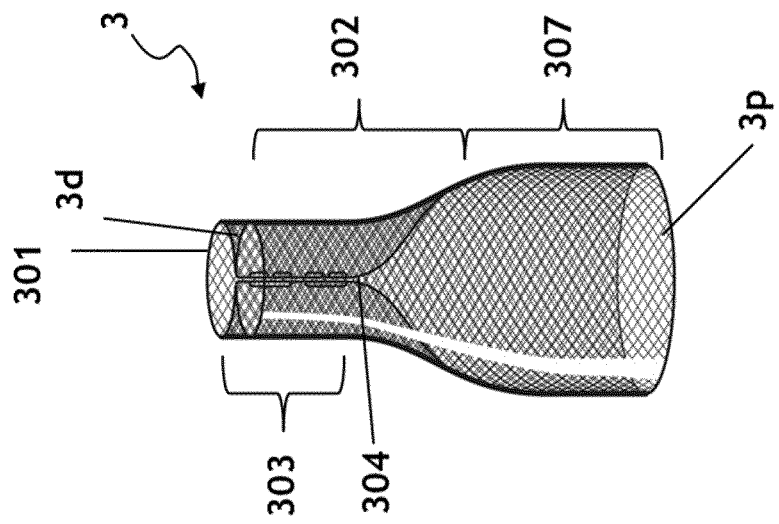
FIGS. 15 and 16 are elevation views of the main body component alone.
Figure 15:
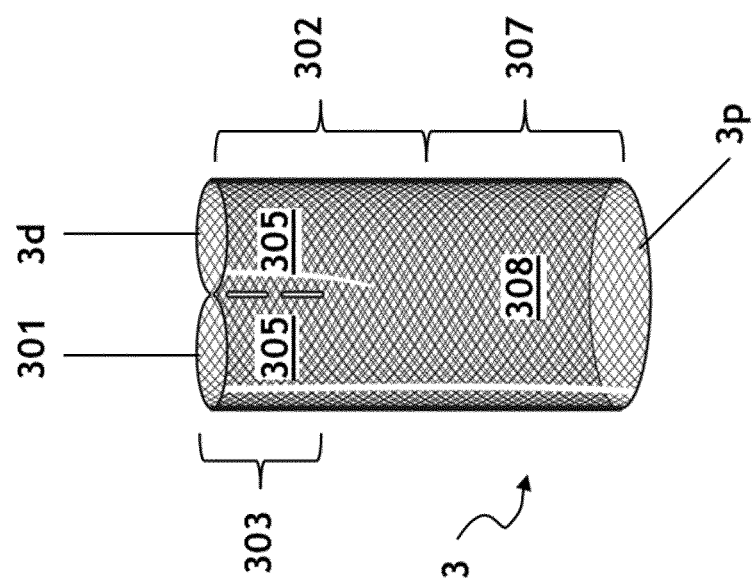

As shown in FIGS. 15 and 16, the main body component 3 comprises, towards a distal end 3*d* of said main body component 3, a concaved portion 302, comprising a double-barrelled portion 303. Middle lines of the concaved portion 302 are concaved along the longitudinal axis of the main body component 3 and define two opposing ridges 304 within an interior of the concaved portion 302. Each ridge 305 partially contacts the other ridge 304. The two opposing ridges 304 define two lumens 305 in the double-barrelled portion 303, each of the two lumens 305 extends along an axis. The axes of the two lumens 305 defines a central plane (CP) which also comprises the axis of the main body component 3.

Figure 18A:
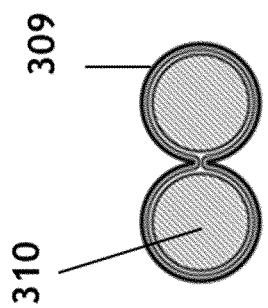
FIG. 18a is a cross view of the mandrel of FIG. 18.
Figure 18:
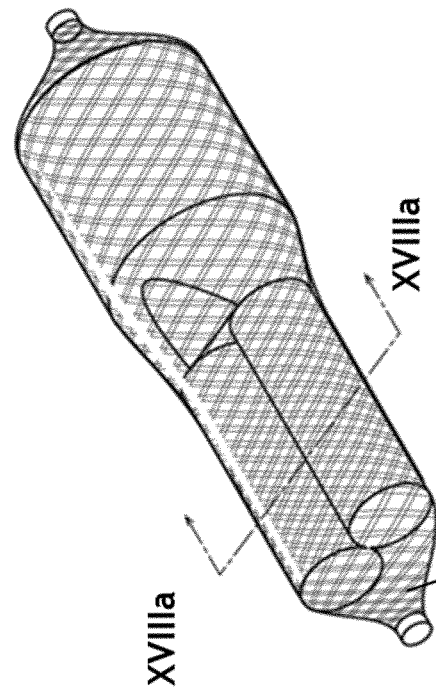
FIG. 18 is a perspective view of the mandrel of FIG. 17 fitted with the formed main body component.
Figure 17:
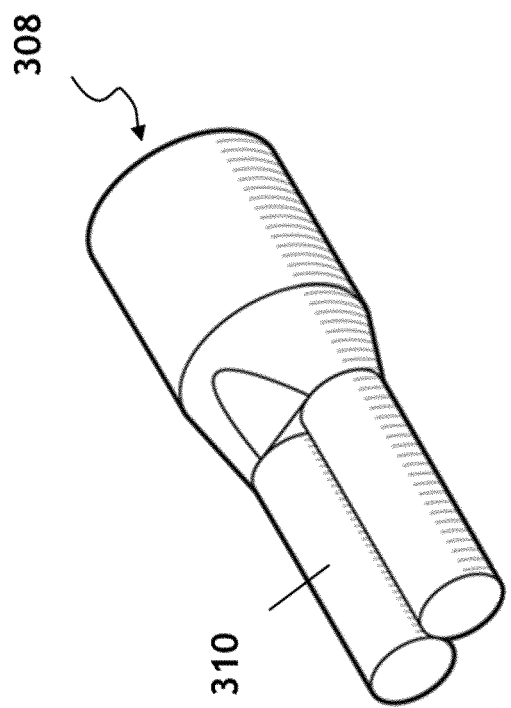
FIG. 17 is a perspective view of a mandrel designed to form the main body component.
Figure 22:
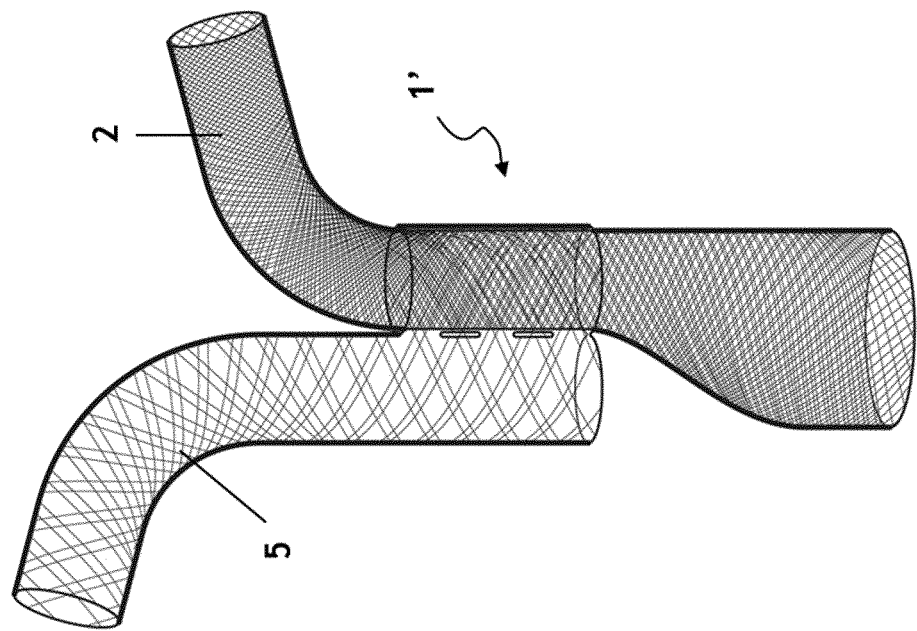
FIGS. 21 and 22 show another embodiment of prosthesis before and after assembled respectively according to the present invention.
Figure 21:
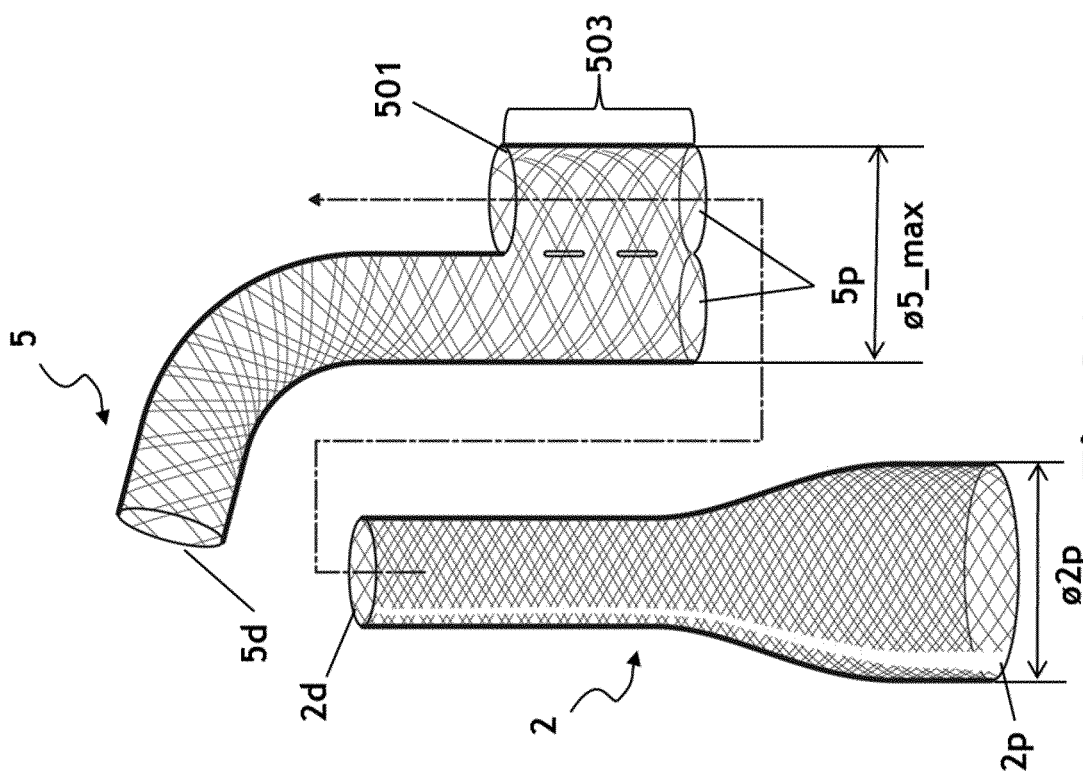
Figure 25:
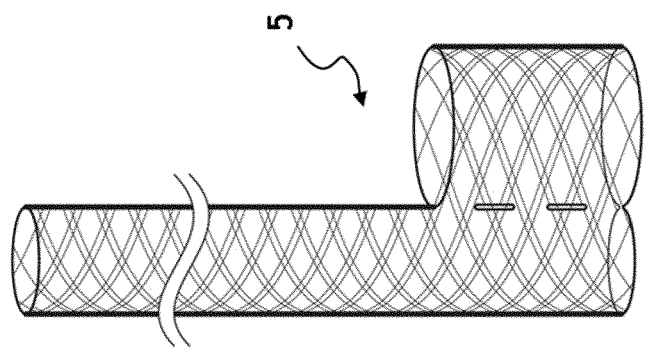
FIGS. 23 to 25 are embodiments of main body component having an extension sleeve as integrated form according to the present invention.
Figure 24:
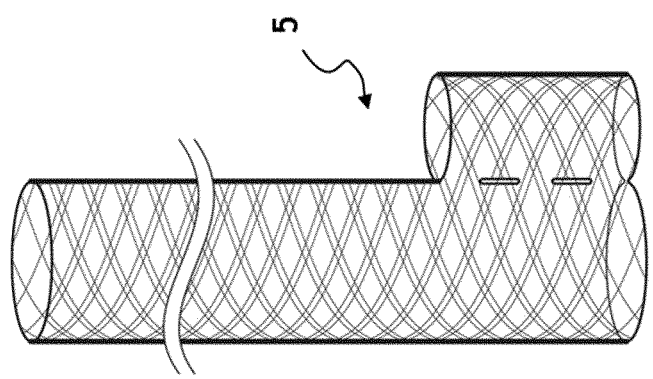
Figure 23:
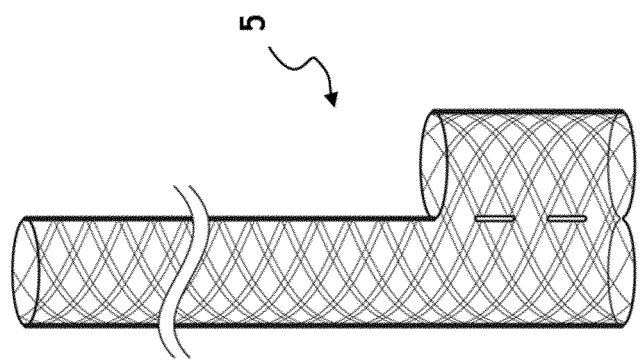

The main body component 3 further comprises, at its proximal end 3*p*, a sealing portion 307 comprising a lumen of cylindrical form with a circular cross-section and a constant diameter, designed to be placed within the CCA so as to "anchor" it and avoid its migration during and after implantation. A proximal part of the filtering sleeve 2 is calibrated so that it is able to be deployed inside the sealing portion 307 of the main body component 3. The neck region 203 of the filtering sleeve 2 is calibrated so that it is able to be deployed inside one of the two lumens 305 of the double-barrelled portion 303 of the main body component 3, as shown in FIGS. 15 and 16. The main body component 3 is preferably formed of a braiding with a plurality of filaments and devoid of any cover layer, preferably formed of a multilayered configuration, more preferably formed of an interlocked multilayer braiding. The main body component 3 can be manufactured by braiding a plurality of wires 309 on a mandrel 308 comprising two legs 310 and by compressing it in order to form the double-barrelled portion 303 as illustrated in FIGS. 17, 18 and 18*a*.

Figure 14:
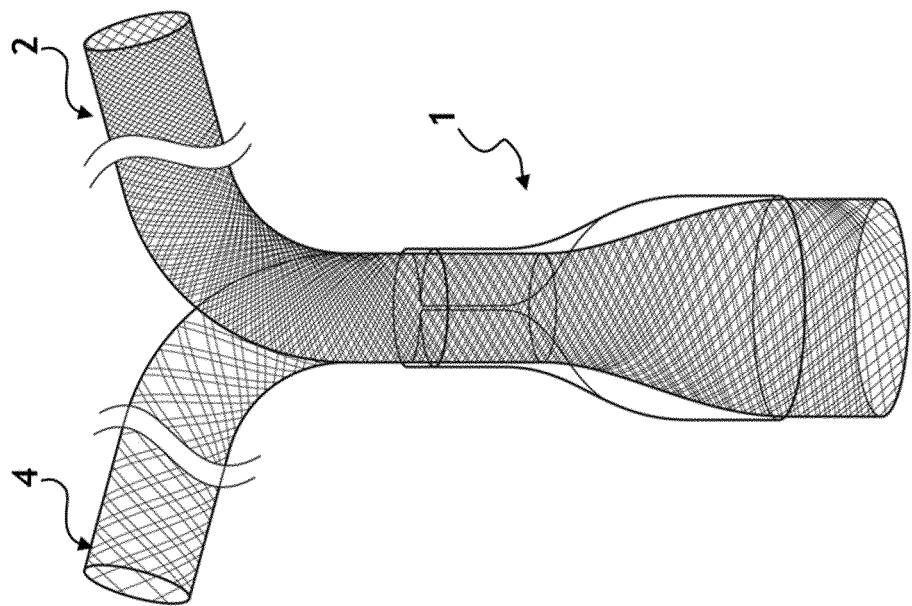
FIGS. 13 and 14 are elevation views of the assembled main body component.
Figure 13:
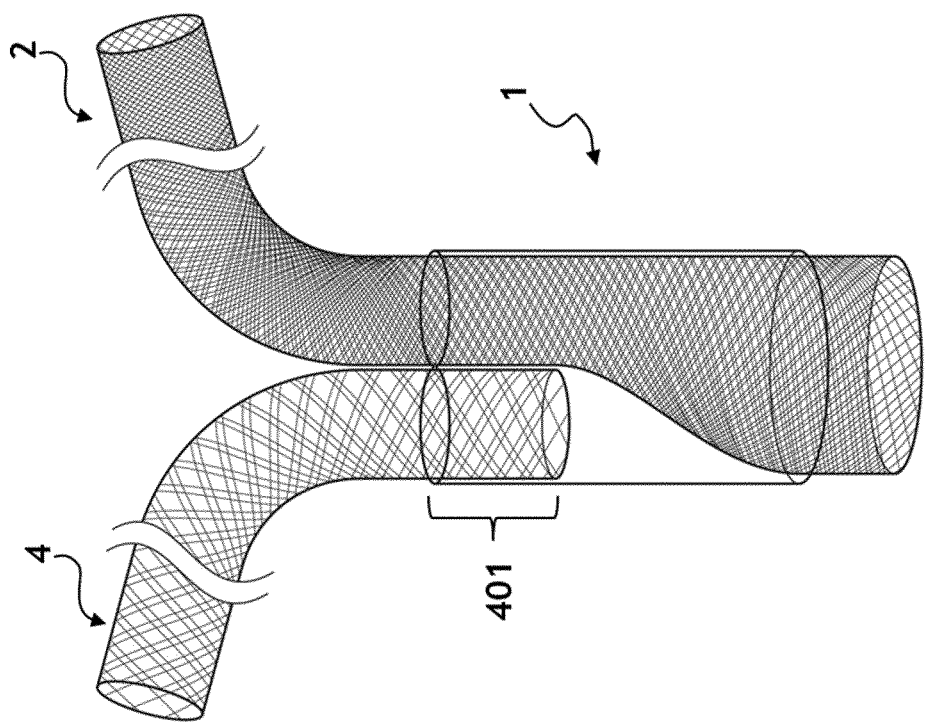

The extension sleeve 4 comprises a tip portion 401 able to be inserted into the other lumen of the double-barrelled portion 303, as shown in FIGS. 13 and 14. The extension sleeve 4 is preferably formed of a braiding with a plurality of filaments and devoid of any cover layer, more preferably having a multilayer configuration, more preferably formed of an interlocked multilayer braiding.

Though the framework is described above as "self-expanding", the main body component 3 and the extension sleeve 4 of the assembly according to the present invention can nevertheless be made out of plastically deformable wires, to be extended by applying to the different parts an internal deforming force, e.g. via inflatable balloons.

Figure 27A:
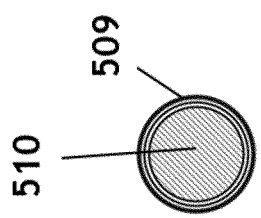
FIG. 27a a cross view of the mandrel of FIG. 27.
Figure 27:
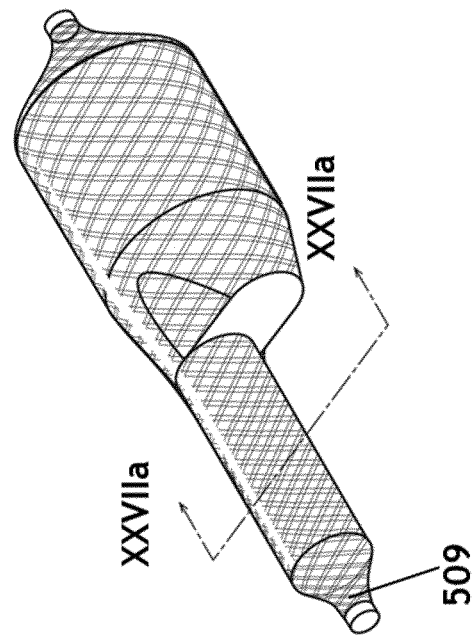
FIG. 27 is a perspective view of the mandrel of FIG. 26 fitted with the formed main body component having an extension sleeve as integrated form.
Figure 26:
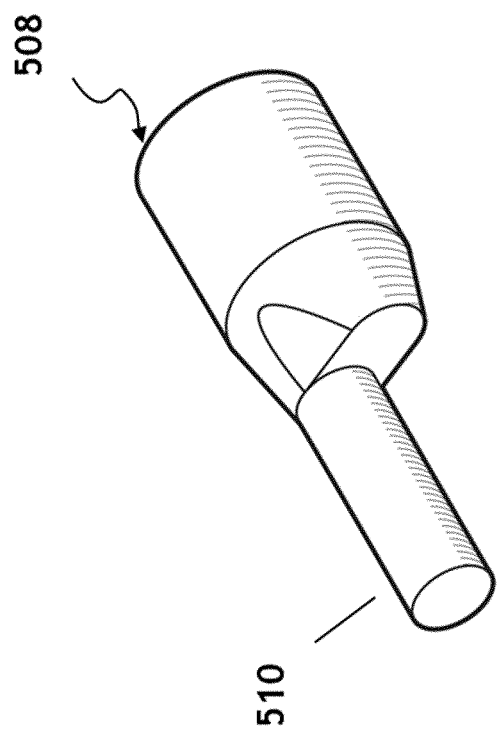
FIG. 26 is a perspective view of a mandrel designed to form the main body component having an extension sleeve as integrated form.

According to another embodiment, shown in FIGS. 19 to 25, the extension sleeve 4 of assembly 1' according to the present invention is integrated to the main body component and forms a luminal extension 502 of an integrated main body component 5 as a single piece. The integrated main component 5 comprises a cylinder body portion 507 that is designed to receive a proximal region of the filtering sleeve 2 therein. The distal region 202 of the filtering sleeves 2 is designed to deploy outside the integrated main component 5 by going out from a filtering sleeve exit 501 of the integrated main body component 5 as shown in FIG. 20. The proximal end diameter ($\varnothing_{2p}$) of the filtering sleeve 2 is designed to be greater than or equal to the maximum diameter ($\varnothing_{5\_max}$) of the integrated main body component 5 in expanded state, so that a portion of the CCA wall will be sealed by the proximal part of the filtering sleeve 2. Thus, the assembly 1' allows the flow of blood, possibly carrying embolic materials ripped out the heart and/or the aorta, to direct into the inner lumen 21 of the filter sleeve 2 from the proximal end 2p while maintaining the "clean" blood flowing into the ICA (which brings the blood toward the brain). The assembly 1' comprising the filter sleeve 2 and the integrated main body component 5 has further advantages that it simplifies the deployment procedure and allows the possibility to use a less bulky delivery system. Accordingly, it reduces risks of complications during an implantation procedure. Said integrated main body component 5 can also be manufactured by braiding a plurality of wires 509 on a mandrel 508 having a leg 510, as shown in FIGS. 26, 27 and 27a.

The double lumens 503 of the integrated main body component 5 as shown in FIGS. 21 to 25 also avoid migration of the filtering sleeve 2 after implantation, as described above. The diameter of the double lumens 503 can differ from each other so as to comply with the various pathologies that can occur in the CCA bifurcation and the ECA.

US Patent Application No. US2006/0015138 discloses that preferred coatings for a filter means should be highly hydrophobic, for example, polytetraethylfluorine (PTFE), polyvinylfluoridene (PVDF), or polyalilene, so as to decrease the degree of friction between the blood and the surface of the device and thus enhance the blood inflow to branches.

Surprisingly, the inventor discovered that combining the above-mentioned structure of braided framework 20, with a coating of a phosphorous-based acid covering the filtering sleeve 2 notably improves embolic rerouting efficacy while keeping an adequate permeability of the braided framework 20 at portions on orifice 36 of the ICA 37. The phosphorous-based acid used can be selected from organic phosphonic acids having the formula $H_2R^1PO_3$ wherein $R^1$ is an organic ligand with a carbon atom directly bonded to phosphorus at its alpha-position. At least one phosphonate moiety of the phosphonate is covalently and directly bonded to the external surface of the metallic substrate in the coating.

In one preferred embodiment, said organic ligand comprises a hydrocarbon chain with between 3 and 16 carbon atoms. The organic ligand is further functionalized at its terminal carbon (i.e. at the opposite end of the alpha-position) so as to increase an interaction between the coating and the embolic material 35 flowing in the CCA. Said functional groups may be a hydroxyl group, a carboxylic group, an amino group, a thiol group, phosphonic group or chemical derivatives thereof. Preferably, the substituent is a carboxylic group, phosphonic group or hydroxyl groups. Said coatings provide improved embolic rerouting efficacy while promoting endothelium formation on the interior wall of the implantable medical device covering the artery wall except portions covering branches' orifices, and keeping an adequate permeability of the braided framework at portions in front of the ICA. Preferably, the number of carbon atoms comprised in the organic ligand is at least 6 and at most 16 as a linier chain, more preferably at least 8 and at most 12. Said phosphonic acid may be selected from a group consisting of 6-phosphonohexanoic acid, 11-phosphonoundecanoic acid, 16-phosphonohexadecanoic acid, 1,8-octanediphosphonic acid, 1,10-decyldiphosphonic acid and (12-phosphonododecyl)phosphonic acid, preferably, 11-phosphonoundecanoic. One of carbon atoms, —($CH_2$)—, of the organic ligand may be substituted by a tertiary amino group, —N($R^2Y$)—. The substituent of tertiary amino group has an alkyl group, —$R^2Y$, the terminal carbon of which is functionalized by carboxylic acid, phosphonic acid or a derivative thereof. Said phosphonic acid comprising the tertiary amino group is preferably selected from a group consisting of N-(phosphonomethyl)iminodiacetic acid and N,N-bis(phosphonomethyl) glycine). In another preferred embodiment, the phosphonic acid may be further functionalized at the alpha-position of the organic ligand by a supplementary phosphonic acid and/or hydroxyl group such as 5-hydroxy-5,5'-bis(phosphono)pentanoic acid. In another preferred embodiment, coatings are formed from germinal bisphosphonates characterized by two C—P bonds located on the same carbon atom defining a P—C—P structure. Said gem-bisphosphonate groups has the general formula (I),

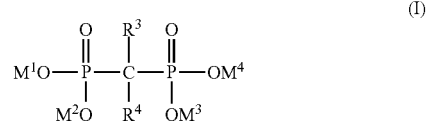

(I)

$R^3$ representing (i) —$C_{1-16}$alkyl unsubstituted or substituted with —COOH, —OH, —$NH_2$, pyridyl, pyrrolidyl or $NR^5R^6$; (ii) —$NHR^7$; (iii) —$SR^8$; or (iv) —Cl; $R^4$ representing —H, —OH, or —Cl; $R^5$ representing —H or —$C_{1-5}$ alkyl; $R^6$ representing —$C_{1-5}$alkyl; $R^7$ representing —$C_{1-10}$ alkyl or —$C_{3-10}$ cycloalkyl; $R^8$ representing phenyl. At least one of $M^1$, $M^2$, $M^3$ and $M^4$ represents any metallic atom in the external surface of the filter sleeve. It means that at least one phosphonate moiety of the bisphosphonate is covalently and directly bonded to the external surface of the metallic substrate in the coating. The bisphosphonate covers at least 50% of the external surface of the metallic substrate as monolayer and as an outermost layer. Preferably $R^3$ represents —$C_{1-16}$ alkyl substituted with —COOH or —OH at the terminal position; and $R^4$ represents —OH. Preferably, said gem-bisphosphonate is etidronic acid, alendronic acid, clodronic acid, pamidronic acid, tiludronic acid, risedronic acid or a derivative thereof.

The invention claimed is:
1. An implantable permanent filter assembly (1) suitable for deployment in a multifurcated vessel dividing a main vessel into at least two branches, wherein said assembly comprises:
 a) a filtering sleeve (2) which is self-expandable from a radially compressed state defining a delivery configuration to a radially expanded state defining a fully expanded configuration; said filtering sleeve comprising, a lumen (21) defined by a wall and extending from a proximal end (2p) to a distal end (2d) of the filtering sleeve, wherein the distal end is configured to extend in one of the at least two branches and the proximal end is configured to extend in the main vessel; said wall having a thickness ($T_2$) and made of a braided framework comprising a plurality of wires (25) which are biocompatible and have a diameter ($\varnothing_{25}$) of at least 20 μm and at most 100 μm; the braided framework comprising a lattice of polygonal openings (26) formed by the braided wires; said polygonal openings, when observed normal with respect to a wall of the filtering sleeve in the fully expanded configuration, being characterized by an inscribed circle (27) having a mean diameter ($\varnothing_{27}$) of at least 50 µm and at most 200 µm; and a surface coverage ratio (SCR) of said braided framework being more than 40% and less than 90% in the fully expanded configuration; and b) an expandable main body component (3) formed of a braiding with a plurality of filaments and devoid of any cover layer, the expandable main body component (3) able to expand from a radially compressed state defining a delivery configuration to a radially expanded state defining a fully expanded configuration, the expandable main body component (3) comprising:

a concaved portion (302) comprising a double-barrelled portion (303) toward a proximal end of the expandable main body component (3);

middle lines of the concave portion being concave along a longitudinal axis of the expandable main body component (3) and defining two opposing ridges (304) within an interior of the concaved portion (302), each ridge (304) partially contacting the other ridge (304), the two opposing ridges (304) defining: a first and second lumens (305) in the double-barrelled portion (303), each of the two lumens (305) extending along an axis; and c) an extension sleeve (4) which is expandable and comprising:

a lumen defined by a wall and extending from a proximal end (4p) to a distal end (4d) of the extension sleeve; and a tip portion (401) able to be inserted into the first lumen of the double-barrelled portion (303), characterised in that:

the braided framework of the filtering sleeve (2) is formed of an interlocked multilayer braiding having a three dimensional structure;

a ratio ($T_2/\varnothing_{25}$) of the thickness ($T_2$) of the wall of the filtering sleeve (2) to the diameter ($\varnothing_{25}$) of the wires (25) is at least 3; and a proximal end diameter ($\varnothing_{2p}$) of the filtering sleeve (2) is equal to or greater than a maximum diameter ($\varnothing_{3\_max}$) defined as a largest diameter of the expandable main body component (3) in a fully expanded state.

2. The implantable permanent filter assembly according to claim 1, wherein the filtering sleeve (2) comprises a proximal region (201) including the proximal end (2p), for implantation in the main vessel such as a common carotid artery, a distal region (202) including the distal end (2d), for implantation in one of the at least two branches such as an external carotid artery, and a neck region (203) extending between the proximal and distal regions (201, 202), the proximal region (201) of the filtering sleeve having a proximal end diameter ($\varnothing_{2p}$) at the level of the proximal end (2p), and a largest neck diameter ($\varnothing_{203}$) defined as a largest diameter at the neck region (203), the proximal end diameter ($\varnothing_{2p}$) being between 1.5 and 3.5 times larger than the largest neck diameter ($\varnothing_{203}$) of the neck region in a fully expanded state.

3. The implantable permanent filter assembly according to claim 1, wherein the interlocked multilayer braiding comprises at least 90 wires; and wherein the ratio ($T_2/\varnothing_{25}$) of the thickness ($T_2$) of the wall to the diameter ($\varnothing_{25}$) of the wires (25) is at least 3.5.

4. The implantable permanent filter assembly according to claim 1, wherein the SCR is more than 50%.

5. The implantable permanent filter assembly according to claim 1, wherein the main body component further comprises at a proximal end (3p) of said expandable main body component (3), a sealing portion (307) comprising a lumen (308) defined by a wall being cylindrical with a circular cross-section and a constant diameter.

6. The implantable permanent filter assembly according to claim 1, wherein the expandable main body component (3) is self-expandable.

7. The implantable permanent filter assembly according to claim 1, wherein the extension sleeve (4) is self-expandable.

8. The implantable permanent filter assembly according to claim 7, wherein the extension sleeve (4) is formed of a braiding with a plurality of filaments and devoid of any cover layer, having a multilayered configuration, preferably formed of an interlocked multilayer braiding.

9. The implantable permanent filter assembly according to claim 1, wherein the wires are coated with a phosphonate containing a hydrocarbon chain comprising 3 to 16 carbon atoms as a linear chain, a phosphorus atom of a phosphonate bonding to the hydrocarbon chain at an alpha-position, said hydrocarbon chain being further functionalized at a terminal position by a carboxylic group, a phosphonic group or a hydroxyl group, the phosphonate being covalently and directly bonded to an external surface of the wire (25) and covering at least 50% of the external surface of the wire as a monolayer and as an outermost layer.

10. The implantable permanent filter assembly according to claim 1, wherein the wires are covered with a gem-bisphosphonate so that at least one phosphonate moiety is covalently and directly bonded to an external surface of the wires (25), and the bisphosphonate covering at least 50% of the external surface of the wires (25) as a monolayer and as an outermost layer.

11. The implantable permanent filter assembly according to claim 10, wherein said gem-bisphosphonate is at least one of: etidronic acid, alendronic acid, clodronic acid, pamidronic acid, tiludronic acid, risedronic acid or a derivative thereof.

12. The implantable permanent filter assembly according to claim 1, wherein the interlocked multilayer braiding comprises at least 100 wires.

13. The implantable permanent filter assembly according to claim 1, wherein the interlocked multilayer braiding comprises at least 160 wires.

14. The implantable permanent filter assembly according to claim 1, wherein the ratio ($T_2/\varnothing_{25}$) of the thickness ($T_2$) of the wall to the diameter ($\varnothing_{25}$) of the wires (25) is at least 4.0.

15. The implantable permanent filter assembly according to claim 1, wherein the ratio ($T_2/\varnothing_{25}$) of the thickness ($T_2$) of the wall to the diameter ($\varnothing_{25}$) of the wires (25) is at least 4.5.

16. The implantable permanent filter assembly according to claim 1, wherein the expandable main body component (3) is formed of a braiding with a plurality of filaments having a multilayered configuration.

17. The implantable permanent filter assembly according to claim 1, wherein the expandable main body component (3) is formed of a braiding with a plurality of filaments that are-formed of an interlocked multilayer braiding.

* * * * *